United States Patent [19]

Kim et al.

[11] 4,139,566

[45] Feb. 13, 1979

[54] SECONDARY ALCOHOL ETHOXYLATE PROCESS

[75] Inventors: Leo Kim; Timm E. Paxson, both of Houston, Tex.

[73] Assignee: Shell Oil Company, Houston, Tex.

[21] Appl. No.: 838,506

[22] Filed: Oct. 3, 1977

[51] Int. Cl.$^2$ .............................................. C07C 41/06
[52] U.S. Cl. .................................... 568/679; 568/619
[58] Field of Search ........................ 260/615 R, 615 B

[56] References Cited

U.S. PATENT DOCUMENTS

| 2,067,385 | 1/1937 | Evans et al. | 260/615 R |
| 2,198,046 | 4/1950 | Vierling | 260/615 R |

FOREIGN PATENT DOCUMENTS

| 2450667 | 10/1973 | Fed. Rep. of Germany. | |
| 51-29413 | 3/1976 | Japan | 260/615 B |
| 6401246 | 8/1965 | Netherlands | 260/615 R |
| 957000 | 4/1964 | United Kingdom | 260/614 A |
| 1176620 | 1/1970 | United Kingdom | 260/614 A |

OTHER PUBLICATIONS

Andrieth, Liquid Sulfur Dioxide, Stauffer Chemical Co., New York, (1969), p. 2.

*Primary Examiner*—Howard T. Mars

[57] ABSTRACT

In the process of reacting olefins with (poly)alkylene glycols in the prsence of acid catalysts to produce the corresponding (poly)alkylene glycol monoalkyl ether, the improvement which comprises carrying out the reaction in the presence of sulfur dioxide.

4 Claims, No Drawings

SECONDARY ALCOHOL ETHOXYLATE PROCESS

BACKGROUND OF THE INVENTION

1. Field of the Invention

This invention relates to a process for the catalytic addition of (poly)alkylene glycols to olefins.

2. Description of the Prior Art

Secondary alcohol ethoxylates generally demonstrate low pour points, good wetting and solubility properties which render them well suited to industrial detergent applications. Conventionally, the materials are obtained by a two-step ethoxylation of the appropriate alcohols as for example, U.S. Pat. No. 2,870,220 issued Jan. 20, 1959. A simpler process going directly from the olefin with good conversion and selectivity is desirable.

German Pat. No. 2,450,667 to Imaizumi et al (Apr. 30, 1975) teaches the reaction of olefins with (poly)alkylene glycols to produce the corresponding glycol monoether in the presence of a strong acid cation exchange resin. The use of an inert hydrocarbon solvent for the reaction is disclosed. The use of a solvent is, however, said not to be necessary and no particular solvents are indicated as being superior to any others.

Netherlands Pat. No. 111,296 discloses the reaction of olefins with polyhydroxy compounds in the presence of acid catalysts such as $BF_3$, sulfuric acids, and aromatic sulfonic acids. The use of a polar solvent is disclosed, particularly one with a dielectric constant of at least 5. Suitable polar organic solvents are disclosed but the superiority over these solvents of liquid $SO_2$ is not noted.

U.S. Pat. No. 2,067,385, issued Jan. 12, 1937, to Evans et al discloses the reaction of polyhydric alcohols and olefins in the presence of acid catalysts, e.g., sulfuric acid and benzene sulfuric acids. No particular effects of solvents are noted.

SUMMARY OF THE INVENTION (Poly)alkylene glycols are added to olefins to produce the corresponding monoalkyl ethers of (poly)alkylene glycol by reacting the (poly)alkylene glycol with the olefin in the presence of an acid catalyst and a liquid sulfur dioxide solvent. The use of a sulfur dioxide solvent over conventional organic solvents provides improved conversion of the olefin and enhanced selectivities to the monoalkyl ether of the (poly)alkylene glycol. One special advantage of the process of this invention is that the particular (poly)alkylene glycol reactant selectively adds cleanly to the reactant olefin without polymerizing to higher glycols.

DESCRIPTION OF THE PREFERRED EMBODIMENTS

The olefins used in this process are linear or branched olefins having from 2 to about 40 carbon atoms. Such compounds are linear or branched and are preferably mono-olefinically unsaturated. The process of this invention is particularly suited to detergent range olefins, i.e., those containing from about 8 to about 20 carbon atoms per molecule. Prior art processes react detergent range olefins with difficulty, particularly detergent range internal olefins. Mixtures of olefins may be utilized.

The (poly)alkylene glycols are dihydric alcohols having 2 to about 30 carbon atoms per molecule. They comprise the simple glycols such as ethylene glycol, propylene glycol, butylene glycol, their homologues and the like, as well as the polyglycols such as diethylene glycol, triethylene glycol, tetraethylene glycol, dipropylene glycol, tripropylene glycol, dibutylene glycol, propylene-ethylene glycol, isobutylene-ethylene glycol and the like. Preferred reactants are the (poly)ethylene and (poly)propylene glycols. (Poly)alkylene glycol is used herein to empass the simple alkylene glycol such as ethylene or propylene glycol as well as the higher polymer analogues, e.g., the polyglycols such as di- and triethylene glycol.

The acid catalysts used in the process are heterogeneous or homogeneous catalysts and are either Bronsted or Lewis acids. The Bronsted acids preferably have a pKa of less than about 2.5. Examples are sulfuric acid, fuming sulfuric acid, fluorosulfonic acid; aromatic sulfonic acids such as benzene sulfonic acid, toluene sulfonic acid and related homologues and analogues; alkyl sulfonic acids including the fluorinated sulfonic acids such as methyl sulfonic acid, perfluoromethylsulfonic acid, perfluoroethyl sulfonic acid, and the like. Heterogeneous catalysts include the acidic ion-exchange resins such as the sulfonated ion-exchange resins; i.e., those containing a plurality of sulfonic acid groups. Examples of such resins include sulfonated styrene-divinylbenzene copolymers, sulfonated phenol-formaldehyde resins and sulfonated benzene-formaldehyde resins. The resin may be of the gel or macroreticular type. Also suitable are the fluroalkyl sulfonic acid resins, especially the fluoroalkyl sulfonic acid resins having the group

as an acidic moiety of the resin, and a Pka of less than about 2.5. The preferred fluorinated alkyl sulfonic acid resins are those having the formula:

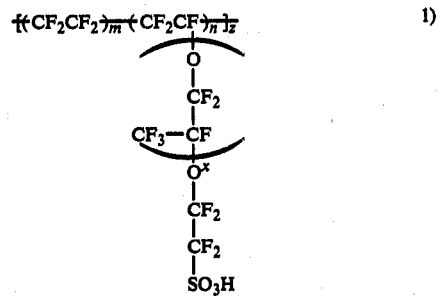

When n is at least one and the sum of m, n, x and z are such that the equivalent weight is 2000 or less, preferably between about 900 and about 2,000, and most preferably between about 960 and about 1200. These resins are further described in U.S. Pat. No. 3,282,875, filed Nov. 1, 1966, which is incorporated herein.

The fluoroalkyl sulfonic acid resins can also have the formulas:

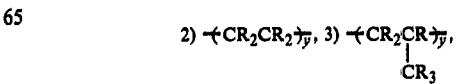

-continued and 4) $+(CR_2CR_2)_a+(CR_2CR)_b]_c$
$\phantom{and 4) +(CR_2CR_2)_a+(CR_2}|$
$\phantom{and 4) +(CR_2CR_2)_a+(CR_2}CR_3$ where R is individually a hydrogen, a fluorine and a —SO$_3$H group and where at least some of the carbons attached to greater than one R simultaneously have one R a —SO$_3$H and one a fluorine and where y and the sum of a, b and c and R are such that the equivalent weight is less than about 2,000, preferably between about 300 and about 1500. A preferred resin is Nafion ®XR resin supplied by E. I. DuPont de Nemours Co., Inc. These resins may be used neat, or supported on a carrier.

The preferred Lewis acids are those having heats of formation with pyridine more exothermic than 7 kcal/mole, preferably more exothermic than 9 kcal/mole. Methods of calculation of heats of formation are given in Drago, et al, J. American Chem. Soc., 93 6014, 1971. Suitable examples are BF$_3$, SbCl$_5$, AlCl$_3$, AlF$_3$, B(CH$_3$)$_3$ and the like.

The process of the invention can also be carried out in the presence of a polar organic co-solvent. Suitable co-solvents generally exhibit a dielectric constant of at least 5 at the reaction temperature. Suitable examples are nitromethane, nitroethane, nitrobenzene, dioxane, 1,2-dimethyloxyethane, furan and sulfolane and its homologues and analogues.

In the process according to this invention, the olefin, glycol, catalyst, sulfur dioxide and optionally co-solvents are brought into contact with each other in a reactor, heated to the reaction temperature at a given sulfur dioxide partial pressure and allowed to react for from about 0.1 to about 30 hours. After cooling, the reactants are worked up by conventional methods to obtain the product alkylene glycol monoalkyl ethers. The use of heterogeneous catalysts allows for the use of flow reactors with liquid hourly space velocities ranging from about 0.01 to about 10 hour $^{-1}$. The reaction temperatures range from about 25° C. to about 250° C., more preferably from about 70° C. to about 200° C. and even more preferably from about 100° C. to about 160° C. The reaction pressure ranges from about 1 atmosphere to about 200 atmospheres. The molar ratio of feed reactants of olefin: (poly)alkylene glycol: catalyst: (hydrogen equivalent): sulfur dioxide typically is about 1:1 to 30:0.01 to 10:1 to 100, and preferably about 1:3 to 10:01 to 4:5 to 30.

The process of this invention will be further described by the following illustrative embodiments which are provided for illustration and are not to be construed as limiting the invention.

ILLUSTRATIVE EMBODIMENTS

Reactions were run in either a 300-ml or a 1-liter, Hastelloy-B autoclave with or without a glass liner. A Teflon ® stirring paddle assembly was employed in conjunction with a Teflon coated or wrapped stirring shaft. The cooling coils and thermocouple well were similarly protected.

The reactor was charged in the following manner: glycol, acid, and finally olefin. The sequence of addition was important to prevent charring of the olefin. The autoclave was sealed, pressure tested with N$_2$, and cooled to −20° C. before admitting the SO$_2$. The reactor was pressurized from 500–1500 psig of N$_2$. When a solvent other than SO$_2$ was utilized, such solvent was added with the olefin.

EXAMPLE 1

A 300-ml, Hastelloy B autoclave with glass liner was charged with 20 gm (124 mmol) of an internal C$_{11}$ and C$_{12}$ olefin mixture, 46.2 gm (744 mmol) of ethylene glycol, 139 gms (2170 mmol) of sulfur dioxide, and 17.5 gms (99 mmol) of benzene sulfonic acid-monohydrate in the manner described above. The reaction was heated at 130° C. for 2 hours. Work-up and gas chromatographic analysis of the reaction mixture gave the distribution: 17.4–18.9 m% conversion of internal olefin, 6.4% selectivity to internal alcohols, 92.4% selectivity to the ethylene glycol adduct, and 1.6% selectivity to the diethylene glycol adduct.

EXAMPLE 2

The experiment of Example 1 was repeated using equivalent molar amounts with a mixed C$_{13}$ and C$_{14}$ internal olefin feed. Analysis of the product showed a conversion of 16–17.1%, 6.5% selectivity to internal alcohols, 91.3% selectivity to ethylene glycol adduct, 1.8% selectivity to diethylene glycol adduct.

EXAMPLE 3

The experiment of Example 1 was repeated using a H$_2$SO$_4$/SO$_3$/H$_3$BO$_3$ catalyst, internal C$_{11}$/C$_{12}$ olefin feedstock, and a mixed sulfolane/SO$_2$ solvent system. The solvent was calculated on the basis of three times the weight of ethylene glycol. A conversion of 6.1-7.0% was obtained with a 7% selectivity to internal alcohols, 86% selectivity to ethylene glycol adduct, and 7% selectivity to diethylene glycol adduct.

EXAMPLE 4

Repeating the reaction of example 1 with the same molar amounts and using SO$_2$ solvent, but varying the acid catalysts gave the following results:

TABLE 1

| Catalyst | Conversion (m%) | Selectivities (m%) | | |
|---|---|---|---|---|
| | | Alcohol | ME* | DE* |
| H$_2$SO$_4$ | 4–6% | 7.3–12 | 88–82 | 4.4–6.0 |
| H$_2$SO$_3$/SO$_3$ | 5–8% | 7.3–12 | 88–82 | 4.0–6.0 |
| H$_2$SO$_4$/SO$_3$H$_3$BO$_3$ | 13.4–14.3 | 7.4 | 88.2 | 4.4 |
| FSO$_3$H/SbF$_5$ | 17–18 | 4.0 | 90.3 | 5.8 |
| FSO$_3$H | 8.8 | 8.2 | 84.1 | 5.1 |
| p-CH$_3$C$_6$H$_4$SO$_3$H . H$_2$O | 16.5–19.5 | 6.0 | 92.0 | 2.0 |
| CH$_3$SO$_3$H | 10.9–11.9 | 6.6 | 91.0 | 2.4 |
| m-HO$_3$SC$_6$H$_4$SO$_3$H | 10.9–11.3 | 13.2–15.3 | 80–77 | 7.9–7.7 |
| BF$_3$ . H$_2$O | 5.8 | 10 | 86 | 4 |
| RBF$_4$ | 10.9 | 15.4 | 84.6 | — |

*ME = ethylene glycol-olefin adduct
*DE = diethylene glycol-olefin adduct

Example 1 was repeated using different solvents. Molar ratios of olefin: p-CH$_3$C$_6$H$_4$SO$_3$H.H$_2$O: ethylene glycol remained at 1:0.8:6. Solvent concentrations were held at 3 times the weight of ethylene glycol. Some solvents were also run with a sulfuric acid catalyst. Time of reaction was 2 hours, temperature 130° C. If the solvent had a boiling point below 130° C., an inert gas cap (N$_2$) was maintained over the reaction.

TABLE 2

| Catalyst | Solvent | Conversion (m%) | Selectivities (m%) | | |
|---|---|---|---|---|---|
| | | | Alcohol | ME* | DE* |
| pCH$_3$C$_6$H$_4$SO$_3$H . H$_2$O | CH$_2$Cl$_2$ | 1–2 | 8–10 | 90–88 | 2–4 |

TABLE 2-continued

| Catalyst | Solvent | Conversion (m%) | Selectivities (m%) Alcohol | ME* | DE* |
|---|---|---|---|---|---|
| pCH$_3$C$_6$H$_4$SO$_3$H . H$_2$O | 1,2-Cl$_2$C$_2$H$_4$ | 3.1 | 8–10 | 90–88 | 2–4 |
| pCH$_3$C$_6$H$_4$SO$_3$H . H$_2$O | (CF$_3$)$_2$CHOH | 9.6 | ~8 | ~88 | ~2 |
| | Some (CF$_3$)$_2$CHO-adduct | | | | |
| pCH$_3$C$_6$H$_4$SO$_3$H . H$_2$O | (CH$_3$)$_2$SO | 0 | — | — | — |
| pCH$_3$C$_6$H$_4$SO$_3$H . H$_2$O | CH$_3$CN | 0 | — | — | — |
| pCH$_3$C$_6$H$_4$SO$_3$H . H$_2$O | CH$_3$NO$_2$ | 4.2 | 8–10 | 90–88 | 2–4 |
| H$_2$SO$_4$ . H$_2$O | C$_4$H$_8$SO$_2$ (sulfolane) | 5.0 | 10–12 | 86–84 | 4–6 |
| H$_2$SO$_4$ . H$_2$O | 3-methyl sulfolane | 4.0–5.0 | 10–12 | 86–84 | 4–6 |
| H$_2$SO$_4$ . H$_2$O | (CH$_3$)$_2$SO$_2$ | 3.0–3.8 | 10–12 | 86–84 | 4–6 |
| H$_2$SO$_4$ . H$_2$O | C$_6$H$_5$NO$_2$/C$_4$H$_8$SO$_2$ | 8–10 | 10–12 | 86–84 | 4–6 |

*ME = ethylene glycol - olefin adduct
*DE = diethylene glycol - olefin adduct

EXAMPLE 5

Example 1 was repeated using a sulfonated styrene-divinylbenzene acid ion exchange resin catalyst Dow - MSC - 1-H in SO$_2$ solvent (olefin:acid ratio 1:0.4). Conversion was 5.3% after a reaction time of 3 hours at 130° C., 6.8% selectivity to internal alcohols, 90.8% selectivity to ethylene glycol adduct, and 2.4% selectivity to the diethylene glycol adduct. The above reaction was repeated using various sulfonated acid ion exchange resins. Olefin:resin ratios (based on milliequivalents of acid sites) were held at 1:0.5 to 1. Reaction conditions were held at 130° C. for 3 hours.

TABLE 3

| Resin | Manufacturer | Conversion (m%) | Selectivities (m%) Alcohol | ME | DE |
|---|---|---|---|---|---|
| XN1010 | Rohm and Haas | ~1.0 | not calculated | | |
| XN1011 | Rohm and Haas | ~1.2 | not calculated | | |
| XN1005 | Rohm and Haas | 6.0 | 23.5 | 76.5 | trace |
| XN1008 | Rohm and Haas | 1.2–1.3 | 25.6 | 74.4 | — |
| Amberlyst 15 | Rohm and Haas | 2.8 | 6.0 | 92.0 | 2.0 |
| Amberlyst 252 | Rohm and Haas | 2.2 | 11.0 | 85.0 | 4.0 |
| Dowex MSC-1-H | Dow | 5.3 | 6.8 | 90.8 | 2.4 |
| Duolite ARC-351 | Diamond Shamrock | 1.2 | 14.8 | 74.7 | 10.5 |
| Zeo-Carb 225 SRC-14 | BDH Chemicals | <1.0 | — | — | — |
| AG-50W-X2 | Bio-Rad | 8.1–10.1 | 9 | 88 | 3.0 |

EXAMPLE 6

A liter autoclave with glass liner was charged with 60 gms (0.713 moles) of mixed internal hexenes, 232 gms (3.74 moles) of ethylene glycol, 25 gms of an H$_2$SO$_4$/SO$_3$/H$_3$BO$_3$ acid mix (1:0.3:0.1), and 300 gms (4.68 moles) of sulfur dioxide. The mixture was heated for 2 hours at 130° C. Upon isolation there was obtained a 44.5% conversion with a 5.5% selectivity to internal hexanols, 84.0% selectivity to the ethylene glycol adduct, 2.9% selectivity to the diethylene glycol adduct, and 8.0% selectivity to the ether C$_6$H$_{13}$OCH$_2$CH$_2$OC$_6$H$_{13}$.

EXAMPLE 7

A series of experiments were performed using 1-dodecene and ethylene glycol as reactants, H$_2$SO$_4$ as catalyst and various solvents. These results are given in Table 1.

TABLE 1

| Ex. | Catalyst | Solvent | T° C | Reaction Time Min. | Conversion 1-dodecene %m | Selectivity$^a$ %m |
|---|---|---|---|---|---|---|
| 1-1$^b$ | H$_2$SO$_4$ | Sulfolane | 150 | 120 | 12 | 75 % I 10% II |
| 1-2$^c$ | H$_2$SO$_4$ | SO$_2$ | 150 | 50 | 35 | >95% I |
| 1-3$^b$ | H$_2$SO$_4$ | CH$_3$CN | 150 | 60 | 3 | >90% I |
| 1-4$^c$ | None | SO$_2$ | 150 | 60 | 0 | — |

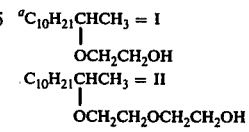

$^a$ C$_{10}$H$_{21}$CHCH$_3$ = I
      |
      OCH$_2$CH$_2$OH

C$_{10}$H$_{21}$CHCH$_3$ = II
      |
      OCH$_2$CH$_2$OCH$_2$CH$_2$OH $^b$ 1.5 g catalyst, 4.0 ml solvent, 1.0 ml 1-dodecene, 2.0 ml ethylene glycol
$^c$ 60 ml SO$_2$, 10 ml 1-dodecene, 20 ml ethylene glycol, 1 ml H$_2$SO$_4$ (when present).

What is claimed is:

1. In the process of reacting olefins with (poly)alkylene glycols at a temperature of from about 25° C. to about 250° C. in the presence of acid catalysts to produce the corresponding (poly)alkylene glycol monoalkyl ether, the improvement which comprises carryout of the reaction in the presence of liquid sulfur dioxide.

2. The process of claim 1 wherein the pressure ranges from about 1 atmosphere to about 200 atmosphere.

3. The process of claim 1 wherein the molar ratio of olefin: poly)alkylene glycol: catalyst (hydrogen equivalent): sulfur dioxide is about 1:1 to 30:0.01 to 10:1 to 100.

4. The process of claim 1 wherein the acids are Bronsted acids having a pKa of less than 2.5 or Lewis acids having a heat of formation with pyridine more exothermic than 9 kcal/mole.

* * * * *